(12) United States Patent
LaRose

(10) Patent No.: US 10,369,292 B2
(45) Date of Patent: Aug. 6, 2019

(54) SYRINGE PLUNGER ASSEMBLIES

(71) Applicant: W. L. Gore & Associates, Inc., Newark, DE (US)

(72) Inventor: Erik M. LaRose, Elkton, MD (US)

(73) Assignee: W. L. Gore & Associates, Inc., Newark, DE (US)

(*) Notice: Subject to any disclaimer, the term of this patent is extended or adjusted under 35 U.S.C. 154(b) by 8 days.

(21) Appl. No.: 15/405,078

(22) Filed: Jan. 12, 2017

(65) Prior Publication Data

US 2017/0203046 A1    Jul. 20, 2017

Related U.S. Application Data

(60) Provisional application No. 62/385,728, filed on Sep. 9, 2016, provisional application No. 62/279,007, filed on Jan. 15, 2016.

(51) Int. Cl.
*A61L 31/04* (2006.01)
*A61M 5/315* (2006.01)

(52) U.S. Cl.
CPC ........ *A61M 5/31515* (2013.01); *A61L 31/048* (2013.01); *A61M 5/31505* (2013.01); *A61M 2005/31508* (2013.01); *A61M 2207/00* (2013.01)

(58) Field of Classification Search
CPC .......... A61M 5/31515; A61M 5/31505; A61M 2207/00; A61M 2005/31508; A61L 31/048
See application file for complete search history.

(56) References Cited

U.S. PATENT DOCUMENTS

| | | | |
|---|---|---|---|
| 5,090,962 | A | 2/1992 | Landry, Jr. et al. |
| 5,374,473 | A | 12/1994 | Knox et al. |
| 5,708,044 | A | 1/1998 | Branca |
| 5,792,525 | A | 8/1998 | Fuhr et al. |
| 6,030,694 | A | 2/2000 | Dolan et al. |
| 6,541,589 | B1 | 4/2003 | Baillie |
| 7,521,010 | B2 | 4/2009 | Kennedy et al. |
| 7,531,611 | B2 | 5/2009 | Sabol et al. |
| 2003/0004491 | A1 | 1/2003 | Tenhuisen et al. |

(Continued)

FOREIGN PATENT DOCUMENTS

| | | |
|---|---|---|
| DE | 2715969 | 2/1978 |
| JP | 2007267906 | 10/2007 |
| WO | WO96/29106 | 9/1996 |

OTHER PUBLICATIONS

International Search Report for PCT/US2017/013290 dated May 9, 2017.

*Primary Examiner* — Lauren P Farrar
(74) *Attorney, Agent, or Firm* — Amy L. Miller

(57) ABSTRACT

A syringe for storing and delivering a fluid that includes (1) a stopper and (2) a plunger rod assembly is provided. The plunger rod assembly includes a plunger rod and a threaded member at a plunger-engaging end. The stopper may be formed of an elastomeric material. The stopper has an exterior surface and an inner cavity. The inner cavity of the stopper may have a generally frustoconical shape with at least one engagement surface. The threaded member contacts at least one engagement surface in the inner cavity of the stopper to support the plunger rod assembly in an integrated, non-threaded engagement with the stopper. In some embodiments, the threaded member is freely rotatable within the inner cavity.

21 Claims, 8 Drawing Sheets

(56) References Cited

U.S. PATENT DOCUMENTS

| | | |
|---|---|---|
| 2005/0029305 A1 | 2/2005 | Brennan |
| 2008/0171199 A1 | 7/2008 | Vaplue et al. |
| 2009/0093602 A1 | 4/2009 | Ford |
| 2010/0185157 A1 | 7/2010 | Kawamura et al. |
| 2010/0248324 A1 | 9/2010 | Xu et al. |
| 2012/0035283 A9 | 2/2012 | Xu et al. |
| 2016/0022917 A1* | 1/2016 | Takai ................ A61M 5/31513 604/222 |
| 2016/0082194 A1* | 3/2016 | Furukawa ........... A61M 5/3129 604/222 |

* cited by examiner

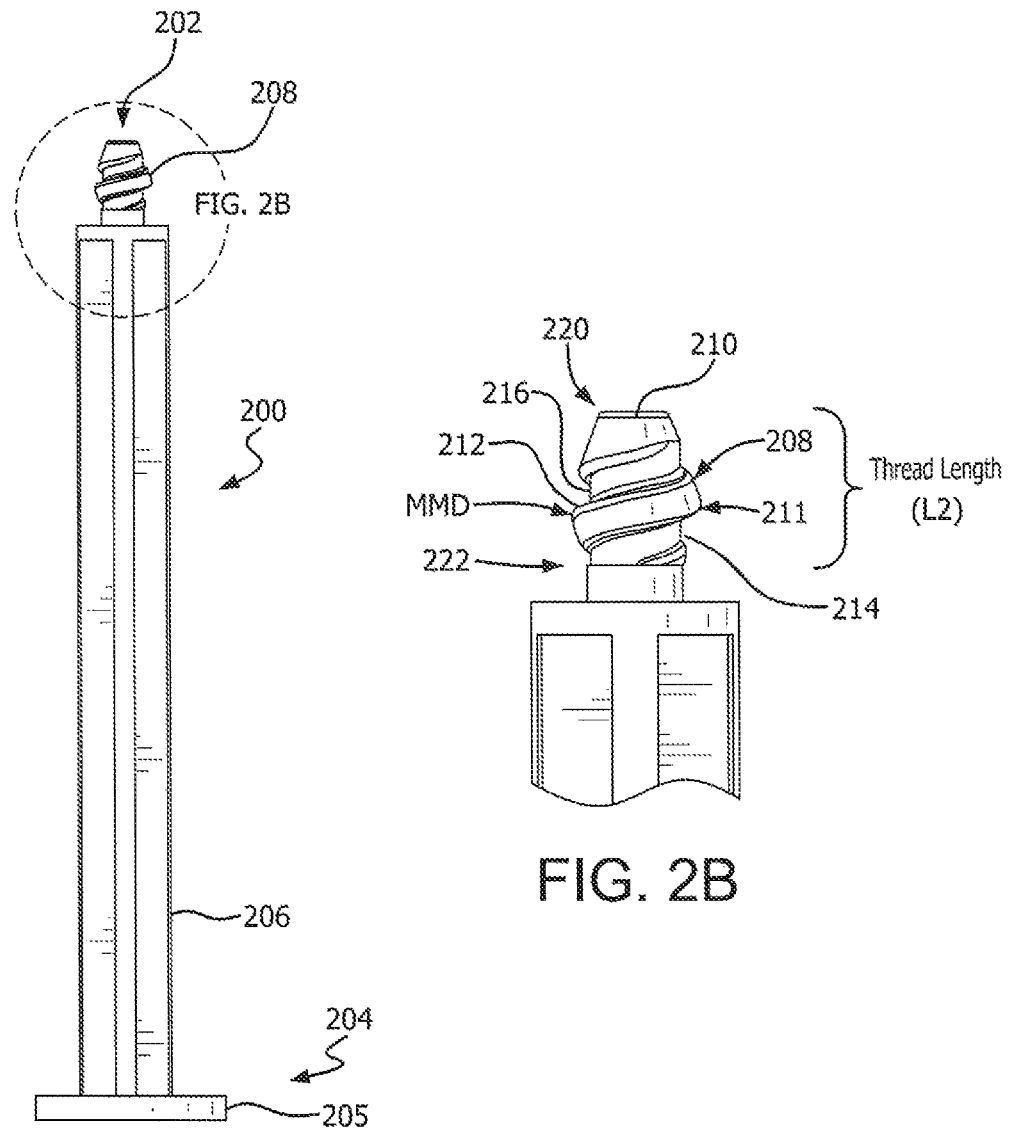

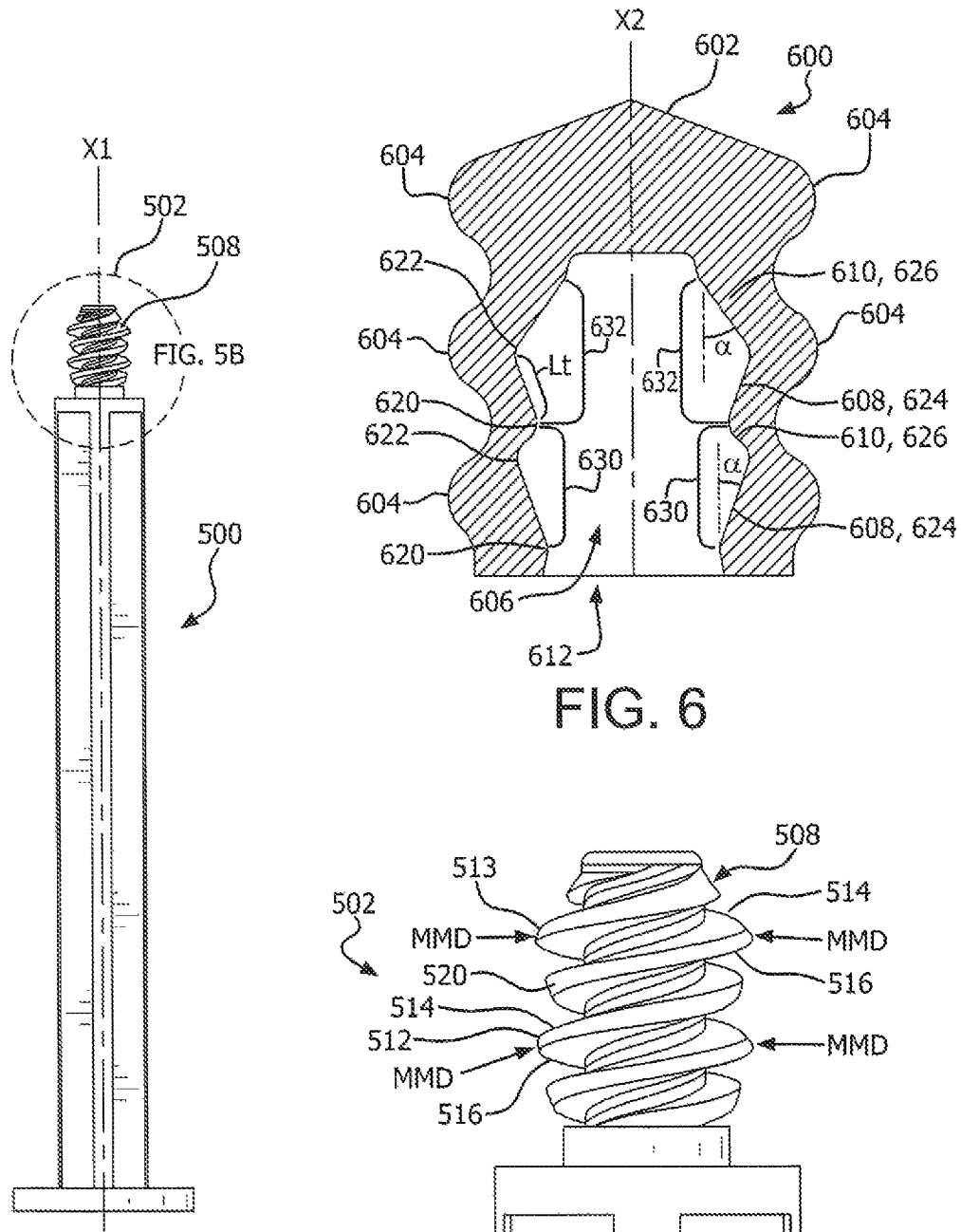

SYRINGE PLUNGER ASSEMBLIES

TECHNICAL FIELD

The present disclosure relates generally to syringes, and more specifically to plunger assemblies that include a stopper having a non-threaded inner cavity with generally smooth walls and a plunger rod assembly having a threaded member and a plunger rod. The stopper is configured to engage a distal end of a plunger rod assembly in an integrated, non-threaded engagement. The threaded member may be freely rotatable within the inner cavity of the stopper.

BACKGROUND

Syringes have traditionally been used in the medical industry to deliver medicaments or to draw biological fluids from a patient. Today, syringes are often prefilled and are used to store medicaments prior to their delivery. Conventionally, a male and female thread or a "push-in" method is used to physically insert a plunger rod into the piston. However, the "push-in" method often requires a high force to insert which results in plunger translation within the barrel if insertion forces are higher than plunger break forces. The male and female thread insertion method causes undesirable plunger rotation within the barrel when the plunger rod reaches the termination of the thread section. Eliminating plunger translation and rotation is desirable to drug manufacturers and is a well-known concern in the pharmaceutical industry because plunger movement within the barrel can potentially breach a sterile barrier of a drug or biologic, thus rendering the syringe useless.

Additionally, syringes typically require the use of silicone oil for rod insertion into the plunger. However, some drug formulations and biologics are sensitive to the presence of silicone oil. The presence of silicone oil anywhere in the plunger system, including the plunger rod may cause leeching or migration of silicone oil to a drug product.

Thus there exists a need in the art for a syringe that has an improved ease of use, that reduces or eliminates plunger translation and rotation, simplifies manufacturing, and eliminates potential leeching and migration of silicone oil.

SUMMARY

One aspect relates to a plunger assembly that includes a plunger rod assembly and a stopper made of an elastomeric material. The stopper has an exterior surface and an inner cavity. The inner cavity of the stopper may include a generally frustoconical portion with at least one engagement surface. The plunger rod assembly includes a plunger rod with a threaded member at a plunger-engaging end. The threaded member contacts the at least one engagement surface to support the plunger rod assembly in an integrated, non-threaded engagement with the stopper. In some embodiments, the exterior surface of stopper includes outwardly extending ribs for engagement with a syringe barrel. In some embodiments, the threaded member is freely rotatable within the inner cavity. In other embodiments, a portion of the inner cavity of the stopper includes at least one non-engaging surface that does not contact the threaded member. In some embodiments, at least a portion of the inner cavity includes at least one non-engaging surface that does not contact the threaded member. In further embodiments, the inner cavity includes a plurality of engagement surfaces and non-engaging surfaces. In some embodiments, each of the engagement surfaces are spaced apart from one another.

A second aspect relates to a syringe assembly includes a cylindrical barrel and a plunger assembly inserted into a receiving end of the cylindrical barrel. The cylindrical barrel has a smooth internal surface. The plunger assembly includes a stopper and a plunger rod assembly. The stopper includes an elastomeric body that has an exterior surface having outwardly extending ribs for engagement with the cylindrical barrel. In addition, the stopper includes an inner cavity having a generally frustoconical portion with an engagement surface. The plunger rod assembly includes a plunger rod and a threaded member at a plunger-engaging end. The threaded member is positioned within the inner cavity of the stopper and is freely rotatable therein. The threaded member may contact the engagement surface of the inner cavity to support the plunger rod assembly in an integrated, non-threaded engagement with the stopper.

A third aspect relates to a plunger assembly for a fluid dispensing syringe that includes a plunger rod assembly and a stopper. The plunger rod assembly includes a plunger rod with a distal end portion that contains a threaded member. The threaded member may have a variable major diameter, which means that the major diameter of the threaded member 208 varies (i.e., changes) along a longitudinal axis defined by the plunger rod. The stopper is formed of an elastomeric body and includes a distal end and a proximal end. The stopper defines a non-threaded, inner cavity that includes first and second frustoconical inner surfaces connecting to an opening. Each frustoconical inner surface is oriented to join each other at their large termination ends. At least one of the frustoconical inner surfaces is configured to engage the threaded member.

A fourth aspect relates to a plunger assembly for a fluid dispensing syringe that includes a plunger rod assembly and a stopper. The plunger rod assembly includes a plunger rod including a distal portion containing a threaded member. The stopper includes an elastomeric body having a distal end and a proximal end. The stopper defines a non-threaded, inner cavity that includes a first pair of frustoconical inner surfaces and a second pair of frustoconical inner surfaces. The first pair of frustoconical inner surfaces is connected to a cavity opening and located proximal to the second pair of frustoconical inner surfaces. At least one of the pairs of frustoconical inner surfaces is configured to engage the threaded member.

A fifth aspect relates to a plunger rod for a fluid dispensing syringe that includes an elongate shaft, a distal end, and a proximal end. The distal end has a threaded member in the form of a helical male thread. The threaded member includes a middle portion between a proximal end and a distal end. Additionally, the threaded member has a profile that includes a variable major diameter having at least one maximum major diameter in the middle portion. The profile forms a shape configured to mate with a non-threaded inner cavity of a stopper.

A sixth aspect relates to a plunger assembly that includes a plunger rod assembly and a stopper made of an elastomeric material. The stopper includes an exterior surface and an inner cavity having a generally frustoconical shape with at least one engagement feature. The plunger rod assembly includes a threaded member at a plunger-engaging end. The threaded member may be non-rotatably positioned within the inner cavity of the stopper. Additionally, the threaded member may contact the engagement feature(s) within the inner cavity to support the plunger rod assembly in a non-threaded engagement in the stopper. In one embodiment, the exterior surface includes a plurality of outwardly extending ribs to engage the syringe barrel. In another embodiment, at least a portion of the inner cavity includes at least one non-engaging feature that does not contact the threaded member.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

FIG. 2A is a side view of an exemplary plunger rod assembly in accordance with at least one embodiment;

FIG. 2B is a magnified view of the distal end portion of the plunger rod assembly of FIG. 2A in accordance with an embodiment;

FIG. 5A is a side view of an exemplary plunger rod assembly in accordance with at least one exemplary embodiment;

FIG. 5B is a magnified view of the distal end portion of the plunger rod assembly of FIG. 5A in accordance with at least one embodiment;

FIG. 6 is a cross-sectional side view of a stopper in accordance with at least one embodiment;

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the figures should not be construed as limiting.

The present disclosure relates to syringes for storing and delivering a fluid, typically for medical use. The syringes provided herein include a plunger rod assembly slidably disposed within a barrel. The plunger rod assembly includes a threaded member and a plunger rod. In various embodiments, the stopper and the rod of the plunger rod assembly provided herein are coupled together in a non-threaded engagement. As used herein, a "non-threaded engagement" is formed when a stopper having a non-threaded cavity engages with a plunger rod having a threaded member.

The design of the syringes provided herein, e.g., syringes having non-threaded engagements, eliminates or minimizes rotation of the plunger rod in the barrel during engagement of the plunger rod with the stopper. Eliminating plunger rotation is desirable to drug manufacturers and is a well-known concern in the industry because plunger movement during insertion into a barrel can potentially breach a sterile barrier of a drug or biologic contained within the syringe barrel.

A non-threaded engagement creates a coupling between a stopper and a plunger rod without generating high coupling forces and retains the capability of retraction due to an interference fit between the non-threaded cavity of the stopper and the threaded member of the plunger rod. The low coupling forces associated with the syringes provided herein eliminate or reduce movement of the stopper during insertion of the plunger rod.

Additionally, the syringes described herein eliminate the need for the use of silicone oil for rod insertion into the stopper, which is used in many existing syringes. Due to the non-uniform profile of the threaded member of the plunger rod, plunger rod insertion into the stopper can be achieved by applying the plunger rod with a combination of torque and axial force against a stopper cavity opening. For at least this reason, silicone oil is not required for rod insertion into the stopper. Some drug formulations and biologics are sensitive to the presence of silicone oil, and by not using silicone oil in the syringe, there is no chance of leeching or migration of silicone oil into a drug product.

Figure 1:
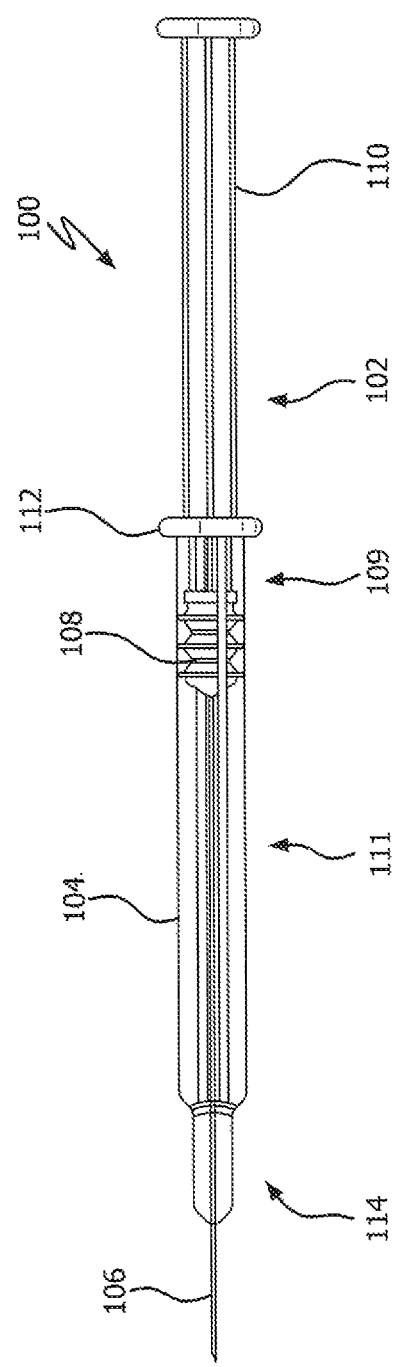
FIG. 1 is a side view of a syringe in accordance with some embodiments provided herein.

Referring to FIG. 1, an exemplary syringe 100 is depicted that includes a plunger rod assembly 102 that is slidably disposed within a barrel 104 for storing and dispensing a fluid (not shown), such as a medicament, from a needle 106. The stopper 108 can be moved from a proximal end to a distal end of the barrel 104 to deliver the fluid contained therein. In some embodiments, the stopper 108 and the plunger rod assembly 102 are separate, but coupleable components. The syringe 100 may be used to store and/or deliver a medical fluid, such as a pharmaceutical composition or a biological substance, into a patient. Alternatively, the syringe 100 may be used to obtain fluids from a patient, such as, for example, a blood sample.

The syringe 100 can be used to hold and optionally store a fluid in a lumen of the barrel 104. The fluid can be stored in the lumen by sealing the proximal end of the barrel 104 with the stopper 108. During use, the syringe 100 can expel the fluid from the barrel 104 when the plunger rod 110 actuates the stopper 108 to slide towards the distal end 114 of the barrel. The stopper 108 can be slidably displaced until a desired amount of the fluid is dispensed or until the stopper 108 has fully translated from the proximal end 109 to the distal end 114 of the barrel 104. The stopper 108 can be translated distally until a tip of the stopper 108 abuts against the distal end 114 of the barrel 104. Alternatively, the syringe 100 may be used to withdraw a biological fluid (e.g., blood) from a patient and optionally store the biological fluid. The stopper 108, when located at the distal end 114 of the barrel 104, can be moved towards the proximal end 109 of the barrel 104 by pulling on the plunger rod 110 to withdraw the fluid. The barrel 104 may be formed of a substantially rigid or hard material, such as a glass material (e.g., a borosilicate glass), a ceramic material, one or more polymeric materials (e.g., polypropylene, polyethylene and copolymers thereof), a metallic material, a plastic material (e.g. cyclic olefin polymers (COC) and cyclic olefin copolymers (COP)), and combinations thereof.

Still referring to FIG. 1, the barrel 104 is a tubular body that includes a proximal end 109, a middle portion 111, and a distal end 114. The proximal end 109 of the barrel 104 includes an opening to the lumen (interior) of the barrel that is adapted for receiving the plunger rod assembly 102, 110. The body of the barrel 104 has an outer diameter and an inner diameter. The proximal end 109 of the barrel 104 may have flanges 112 that radially extend away from the exterior surface of the barrel 104 for convenient gripping during use. The inner diameter of the barrel 104 at the proximal end 109 and middle portion 111 may be generally constant. Near the distal end 114, the inner and outer diameters of the barrel 104 may be tapered to smaller diameters to facilitate the connection of the needle 106 and the barrel 104.

In some embodiments, the distal end 114 of the barrel 104 includes a luer connector (not illustrated), e.g., a luer-lock fitting. The luer connector can be configured to receive needle tip components such that several different needle sizes can be interchangeably used with a single barrel 104 in a syringe 100. Alternatively, a luer connector can be utilized in place of a needle in a needless system.

Referring to FIGS. 2A and 2B, an exemplary plunger rod assembly 200 includes a distal end 202 coupleable to a stopper, a proximal end 204 including a thumb press 205, and an elongate shaft 206 extending between the distal end 202 and proximal end 204. The distal end 202 of the plunger rod assembly 200 includes a threaded member 208 that is coupleable to a plunger rod 206.

The plunger rod 206 of the plunger rod assembly 200 has a length suitable for translating the threaded member 208 to the distal end of a barrel (not shown). In some embodiments, the length of the plunger rod 206 is adapted to allow the thumb press 205 to come in contact with flanges at the distal end of the barrel, such as, for example, flanges 112 at the distal end of barrel 104 of FIG. 1. The thumb press 205 may be formed of numerous sizes and shapes to accommodate different patient groups and/or to interface with needlestick safety devices. The plunger rod 206 can have various cross-sectional shapes. In some embodiments, as shown in FIG. 2B, the cross-section of the plunger rod 206 may be cross-shaped. In some embodiments, the plunger rod 206 may include a circular, a rectangular, a triangular, or a square cross-sectional shape. The plunger rod 206 can be made of a metal or a plastic material, such as thermoplastic polymer. Suitable materials that can be used to construct the plunger rod 206 include, but are not limited to, polypropylene, polystyrene, and polycarbonate.

The plunger rod assembly 200 includes a threaded member 208 that has a middle portion 211 extending between the proximal end 220 and the distal end 222 of the threaded member 208. The threaded member 208 may have a blunt end 210 at proximal end 220, such as is shown in FIGS. 2A and 2B. In some embodiments, the blunt end 210 of the threaded member 208 prevents or minimizes damage that might occur when the distal end 202 of the plunger rod assembly 200 is inserted into a stopper. The blunt end 210 also allows the plunger rod assembly 200 to rotate freely when the threaded member 208 is coupled to a stopper. In some embodiments, the distal end 220 of the threaded member 208 may include a blunt end with no tapered section, such as a cylindrical blunt end (not shown).

The length of the threaded member 208 between the distal end 222 and the proximal end 220 may range between 1 millimeter (mm) and 13 mm, including all ranges and values therebetween. In some embodiments, the length of the threaded member 208 between the distal end 222 and the proximal end 220 may range from about 1 mm to about 6 mm, from about 2 mm to about 5 mm, from about 3 mm to about 4 mm, or from about 4 mm to 5 mm. Suitable threaded member 208 lengths can range from about 1 mm to about 2 mm, from about 2 mm to about 3 mm, from about 3 mm to about 4 mm, from about 4 mm to about 5 mm, from about 5 mm to about 6 mm, from about 5 mm to about 7 mm, from about 1 mm to about 3 mm, from about 1 mm to about 4 mm, from about 1 mm to about 5 mm, from about 1 mm to about 6 mm, from about 2 mm to about 4 mm, from about 2 mm to about 5 mm, from about 2 mm to about 6 mm, from about 3 mm to about 7 mm, from about 3 mm to about 6 mm, from about 4 mm to about 7 mm, from about 6 mm to about 7 mm, from about 8 mm to about 10 mm, or from about 10 mm to about 13 mm.

In various embodiments provided herein, the threaded member 208 may be configured to mate with an inner cavity of a stopper. In some embodiments, the threaded member 208 may be coupled to a non-threaded inner cavity of a stopper. In some embodiments, the threaded member 208 is coupled to a cavity having a generally frustoconical shape within a stopper. In some embodiments, a non-threaded inner cavity may include other geometries such as, but not limited to, spherical, toroidal, cylindrical and polyhedral shaped inner walls. The threaded member 208 may be configured such that the threaded member 208 is engaged (i.e. in contact with) or non-engaged (i.e. not in contact with) with a portion of the stopper that forms a non-threaded engagement. It is to be noted that the inner cavity are also compatible with plunger rod assemblies that do not contain a threaded member, such as push-in styles.

The threaded member 208 may include a helical male thread. Types of male threads suitable for use with the threaded member 208 include, but not limited to, V-shaped, square-shaped, acme, buttress and knuckle male threads. The male thread of the threaded member 208 can include one, two, three, four, five, or six or more turns along the length of the threaded member 208. In some embodiments, the threaded member 208 may include a helical male thread having a single-start thread or a multi-start thread design.

The profile (i.e. major diameter) of the threaded member 208 can vary along a longitudinal direction. In some embodiments, as will be discussed further, the profile of the threaded member 208 may be shaped complementarily to the cavity shape of a stopper. In the embodiment shown in FIG. 2B, the threaded member 208 has a variable major diameter, which means that the major diameter of the threaded member 208 changes along a longitudinal axis defined by the plunger rod 206 of the plunger rod assembly 200. In some embodiments, the threaded member 208 defines a maximum major diameter (MMD) in the middle portion 211 of the threaded member 208. In particular, the maximum major diameter of the threaded member 208 may form a crest peak 212 in the middle portion 211, in which the crest peak 212 defines a portion of the threaded member 208 having a diameter larger than adjacent portions of the threaded member 208. In some embodiments, the crest peak 212 is located near or at the middle portion 211. In some embodiments, the crest peak 212 is located distal to the middle portion 211 of the threaded member 208. In other embodiments, the crest peak 212 is located proximal to the middle portion 211 of the threaded member 208. Adjacent to the crest peak 212, the diameter of the threaded member 208 decreases, creating transitional threaded regions 214, 216. The crest peak 212 can include a proximal and a distal transitional threaded region 214, 216, respectively. For instance, a helical male thread at the proximal transitional threaded region 214 can form an engagement contour that mates with a complementary inner surface within the inner cavity of a stopper that couples the plunger rod assembly 200 to the stopper in a non-threaded engagement.

The transitional threaded regions 214, 216 can, in some embodiments, have a thread length (L2) from about 0.25 mm to about 7 mm, including all ranges and values therebetween. In some embodiments, the thread length of the transitional threaded regions 214, 216 may range from about 0.25 mm to about 0.5 mm, from about 0.5 mm to about 1 mm, from about 1 mm to about 1.5 mm, from about 1.5 mm to about 2.0 mm, from about 2.0 mm to about 2.5, from about 2.5 mm to about 3.0 mm, from about 3.0 mm to about 3.5 mm, from about 3.5 mm to about 4.0 mm, from about 4.0 mm to about 4.5 mm, from about 4.5 mm to about 5.0 mm, from about 5.0 mm to about 5.5 mm, from about 5.5 mm to about 6.0 mm, or from about 5 mm to about 7 mm.

The diameter of the threaded member 208 may range from about 1 mm to about 6 mm, including all ranges and values therebetween. In some embodiments, the diameter of the threaded member 208 may range from about 1.0 mm to about 6 mm, from about 1.5 mm to about 6 mm, from about, from about 2 mm to about 6 mm, from about 3 mm to about 5 mm, or from about 3 mm to about 4 mm. In some embodiments, the major diameter may range from about 1.5 mm to about 2 mm, from about 2 mm to about 3 mm, from about 3 mm to about 4 mm, from about 3.5 to about 4 mm, from about 4 mm to about 5 mm, from about 5 mm to about 6 mm, from about 1 mm to about 3 mm, from about 1.5 mm to about 4 mm, from about 1.5 mm to about 5 mm, from about 1.5 mm to about 6 mm, from about 2 mm to about 4 mm, from about 2 mm to about 5 mm, from about 2 mm to about 6 mm, from about 3 mm to about 5 mm, from about 3 mm to about 6 mm, or from about 4 mm to about 6 mm.

The maximum major diameter (MMD) of the threaded member 208 may range from about 2 mm to about 6 mm, including all ranges and values therebetween. In some embodiments, the MMD of the threaded member 208 may range from about 1.0 mm to about 6 mm, from about 1.5 mm to about 6 mm, from about 2 mm to about 6 mm, from about 3 mm to about 5 mm, or from about 3 mm to about 4 mm. In some embodiments, the MMD may range from about 2 mm to about 3 mm, from about 3 mm to about 4 mm, from about 4 mm to about 5 mm, from about 5 mm to about 6 mm, from about 2 mm to about 4 mm, from about 2 mm to about 5 mm, from about 2 mm to about 6 mm, from about 3 mm to about 5 mm, from about 3 mm to about 6 mm, or from about 4 mm to about 6 mm.

In some embodiments, the minimum diameter of threaded member 208 ranges from about 1 mm to about 6 mm, including all ranges and values therebetween. The minimum diameter of the threaded member 208 may range from about 1.0 mm to about 6.0 mm, from about 1.0 mm to about 5.5 mm, from about 1.0 to about 5 mm, from about 1.0 mm to about 4.0 mm, from about 1.0 mm to about 3 mm, from about 1.0 mm to about 2.0 mm, from about 1.0 mm to about 1.5 mm, or from about 1.0 mm to about 1.3 mm. In some embodiments, the threaded member 208 may have a maximum major diameter of about 1.1, about 1.2, about 1.3, about 1.4, about 1.5, about 1.70, about 1.75, about 2, about 2.25, about 2.5, about 2.75, about 3, about 3.5, about 4, about 4.5, about 5, about 6, about 7, about 8, about 9, or about 10 times greater than the minimum diameter. In some embodiments, the ratio of the minimum diameter to the maximum major diameter ranges from about 1:1 to about 1:2, from about 1:2 to about 1:3, from about 1:3 to about 1:4, from about 1:4 to about 1:5, from about 1:5 to about 1:6, from about 1:6 to about 1:7, from about 1:7 to about 1:8, from about 1:8 to about 1:9, or from about 1:9 to about 1:10.

Figure 3A:
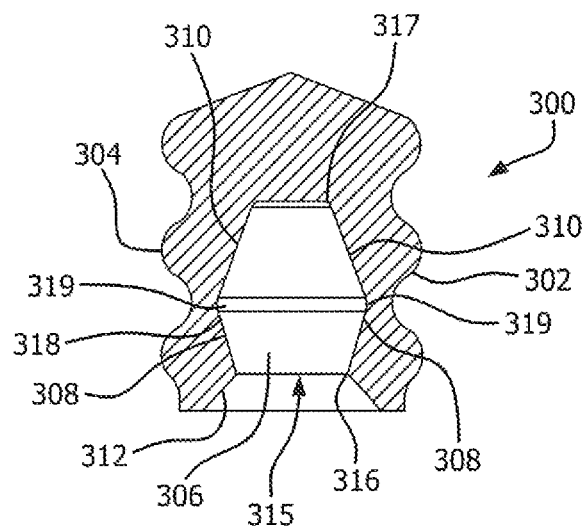
FIG. 3A is a cross-sectional view of an exemplary stopper that has a necked opening in accordance with some embodiments.

Referring now to FIG. 3A, an exemplary stopper 300 is depicted that is compatible with the plunger rod assembly 200 shown in FIGS. 2A and 2B. The stopper 300 may include an elastomeric body 302 defined by an exterior surface having one or more rib(s) 304 and an interior surface that defines an inner cavity 306. The elastomeric body may be formed of a variety of elastomeric materials, such as, but not limited to, rubbers constructed from butyl, bromobutyl, chlorobutyl, silicone, nitrile, styrene butadiene, polychloroprene, ethylene propylene diene, fluoroelastomers, thermoplastic elastomers (TPE), thermoplastic vulcanizates (TPV), silicon, and materials sold under the trade name VITON® and combinations and blends thereof. Exemplary elastomeric materials include, but are not limited to, butyl rubber, bromobutyl rubber, chlorobutyl rubber, silicone, nitrile, styrene butadiene, polychloroprene, ethylene propylene diene, fluoroelastomers and combinations thereof. As will be described in further detail hereafter, the inner cavity 306 is a non-threaded cavity having generally smooth inner walls configured to engage the threaded member 208 of the plunger rod assembly 200 in a non-threaded engagement.

The stopper 300 can have an exterior shape that forms a slidable seal with a syringe barrel. For example, as shown in FIG. 3A, the elastomeric stopper 300 may include one or more outwardly extending ribs 304 that engage with a syringe barrel, such as, for example, barrel 104 of FIG. 1. The ribs 304 of the stopper 300 can have an outer diameter that is greater than an inner diameter of the syringe barrel to facilitate adequate sealing between the stopper 300 and the syringe barrel. Because the ribs 304 of the stopper 300 can elastically deform, the stopper 300 may be inserted inside the barrel and slidably move within the barrel despite the ribs 304 having a larger diameter than that of the inside of the barrel, which may be lubricant-free.

Still referring to FIG. 3A, the inner cavity 306 is sized and shaped to receive the distal end of a plunger rod assembly, such as, for example, the threaded member 208 depicted in FIGS. 2A and 2B. In some embodiments, the inner cavity 306 may have a shape that is generally complementary to the shape of the threaded member 208. In other embodiments, the inner cavity 306 may be a non-threaded cavity having smooth inner walls configured to engage the threaded member 208 of the plunger rod assembly 200 in an integral, non-threaded engagement. In the exemplary stopper 300 shown in FIG. 3A, the inner cavity 306 includes two adjacent frustoconical surfaces that connect to form a necked opening 312 at the proximal end of the stopper 300. In some embodiments, inner cavity 306 may include other geometries such as, but not limited to, spherical, toroidal, cylindrical and polyhedral shaped inner walls.

In some embodiments, the inner cavity 306 includes first and second frustoconical inner surfaces 308, 310, in which the first frustoconical inner surface 308 is located proximal to the second frustoconical inner surface 310 and distal to the necked opening 312. Each frustoconical inner surface 308, 310 may include a small termination end 316, 317 and the large termination ends 319. The frustoconical inner surfaces 308, 310 may have a tapered surface extending between the small and large termination ends. Additionally, the frustoconical inner surfaces 308, 310 may be oriented to join one another at the large termination ends 319. For instance, the first and second frustoconical inner surfaces 308, 310 may join to form large termination ends 319. Opposing large termination ends 319 define the maximum inner diameter of the inner cavity 306. In some embodiments, the first and second frustoconical inner surfaces 308, 310 form a substantially diamond-shaped or a hexagonal cross-sectional shaped inner cavity 306 within the stopper 300 (not illustrated). In some embodiments, the inner cavity 306 can include a proximal inner wall having a frustoconical shape and a distal inner wall having a cylindrical shape (not illustrated).

The inner cavity 306 of the stopper 300 may be configured to obtain a desired predetermined maximum retention force, which is the amount of force required to separate a stopper 300 from a threaded member (e.g., the threaded member 208 depicted in FIG. 2A) of the plunder rod assembly 200. The threaded member may therefore be removed from the stopper 300 when the threaded member is pulled away from the stopper 300 with a force that exceeds the predetermined maximum retention force. In some embodiments, the threaded member may elastically deform the walls of the inner cavity 306, e.g., one or more of the frustoconical inner surfaces 308, 310, as the threaded member is being pulled out of the stopper 300.

In some embodiments, the predetermined maximum retention force between a threaded member and the stopper 300 can range from about 2 Newtons (N) to about 50 N, including all ranges and values therebetween. In some embodiments, the predetermined maximum retention force between a plunger rod and the stopper 300 may range from about 2 N to about 40 N, from about 3 N to 35 N, from about 4 N to 30 N, from about 5 N to about 25 N, from about 6 N to about 20 N, from about 7 N to about 15 N, from about 8 N to about 10 N, or from about 9 N to about 10 N. In some embodiments, the predetermined maximum retention force between a plunger rod and the plunger 300 may range from about 2 N to about 15 N, from about 3 N to about 15 N, from about 8 N to about 12 N.

In some embodiments, the necked opening 312 of the stopper 300 can be sized and shaped to receive a threaded member, such as the threaded member 208 depicted in FIG. 2B. In some embodiments, the inner diameter of the necked opening 312 has a larger diameter at the proximal end of the stopper 300 that tapers to a smaller diameter within the inner cavity 306. For example, as shown in FIG. 3, the inner cavity 306 may have an engagement orifice 315 defined as a region having the smallest diameter (i.e., minimum diameter) in the inner cavity 306. In some embodiments, the diameter of the engagement orifice 315 may range from about 1.0 mm to about 6.0 mm, from about 1.0 mm to about 5.5 mm, from about 1.0 to about 5 mm, from about 1.0 mm to about 4.0 mm, from about 1.0 mm to about 3 mm, from about 1.0 mm to about 2.5 mm, from about 1.5 mm to about 2.5 mm, or from about 1.0 mm to about 2.3 mm. In some embodiments, the engagement orifice 315 may be located where the first frustoconical inner surface 308 connects to the necked opening 312, as shown in FIG. 3A. In other embodiments, the necked opening 312 may be tapered to allow a threaded member of a plunger rod assembly to pass through the engagement orifice 315 when the threaded member is pushed and/or torqued against the engagement orifice 315.

Figure 3B:
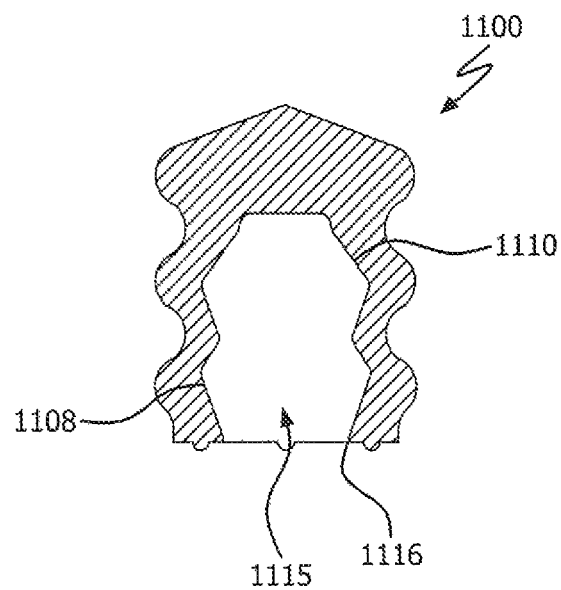
FIG. 3B is a cross-sectional view of an exemplary stopper that does not have a necked opening in accordance with some embodiments.

In some embodiments, shown, for example, in FIG. 3B, the stopper 1100 does not have a necked opening. Instead, the stopper 1100 may have a first frustoconical inner surface 1108 that abuts the proximal end. In such embodiments, the first frustoconical surface 1108 may be located proximal to the second frustoconical inner surface 1110 such that the small termination end 1116 of the first frustoconical inner surface 1108 is located at the proximal end of the stopper 1100. The engagement orifice 1115 therefore, in some embodiments, may be formed by the smaller termination end 1116 of the first frustoconical inner surface In some embodiments, the stopper may include an outer layer material or a coating to reduce friction as the stopper slides within a syringe barrel. Suitable materials that may be used as an outer layer include, but are not limited to, polytetrafluoroethylene (PTFE), expanded polytetrafluoroethylene (ePTFE), densified expanded polytetrafluoroethylene, fluorinated ethylene propylene (FEP), perfluoroalkoxy (PFA), tetrafluoroethylene hexafluoropropylene vinylidene fluoride terpolymer (THV), polyethylene, polypropylene, polyvinylidene fluoride, polyvinylfluoride, perfluoropropylevinylether, perfluoroalkoxy polymers, and copolymers and combinations thereof The outer layer may also include a composite fluoropolymer film having a barrier layer and a porous layer. The porous layer, for example, maybe formed of ePTFE or other porous expanded and fibrilizing fluoropolymers (for example, ePTFE as taught in U.S. Pat. No. 6,541,589 to Baille). The ePTFE layers may be filled with an organic or inorganic material to provide color, lubricity, or other function.

As discussed above, in a some embodiments, the outer layer may include a densified expanded fluoropolymer, such as, but not limited to, a densified expanded polytetrafluoroethylene (ePTFE). A densified ePTFE film may be prepared in the manner described in U.S. Pat. No. 7,521,010 to Kennedy, et al., U.S. Pat. No. 6,030,694 to Dolan et al., U.S. Pat. No. 5,792,525 to Fuhr et al., or U.S. Pat. No. 5,374,473 to Knox et al. Expanded copolymers of PTFE, such as are described in U.S. Pat. No. 5,708,044 to Branca, U.S. Pat. No. 6,541,589 to Baillie, U.S. Pat. No. 7,531,611 to Sabol et al., U.S. Patent Publication No. 2009/0093602 to Ford, U.S. (Ser. No. 12/410,050) to Xu, et al., and U.S. Patent Publication No. 2010/0248324 to Xu et al. may be utilized if they are densified.

In some embodiments, the outer layer may also include an expanded polymeric material including a functional tetrafluoroethylene (TFE) copolymer material having a microstructure characterized by nodes interconnected by fibrils, where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. The functional TFE copolymer material may be prepared, for example, according to the methods described in U.S. Patent Publication No. 2010/0248324 to Xu et al. or U.S. Patent Publication No. 2012/035283 to Xu et al.

Figure 4:
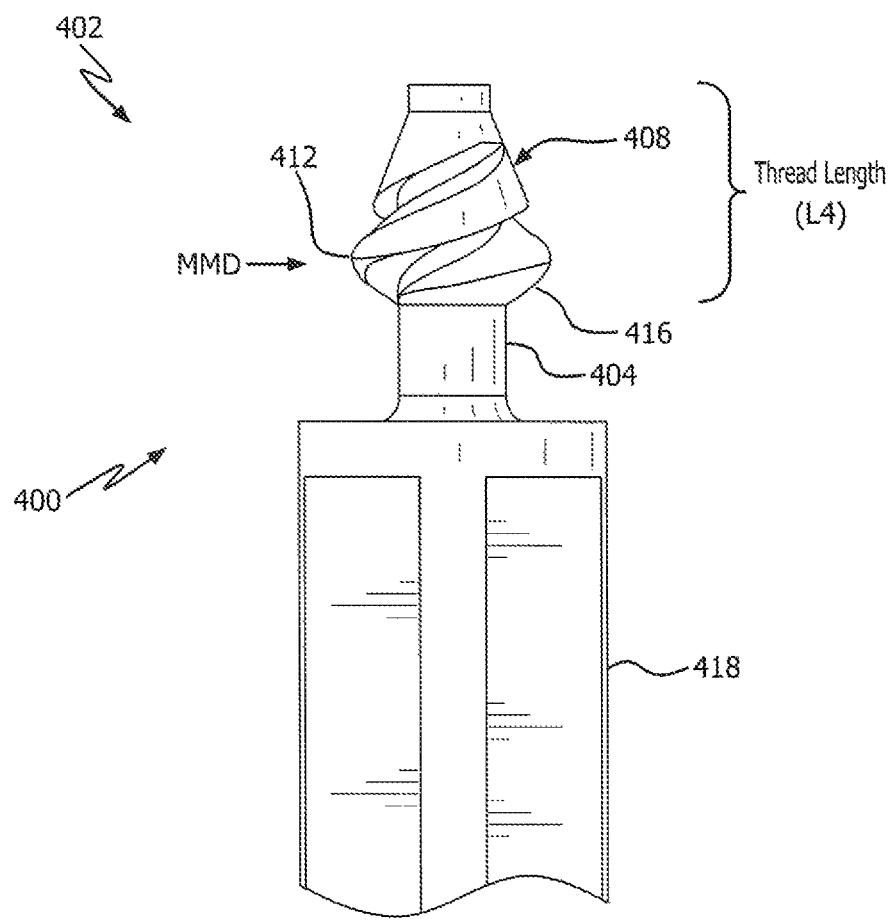
FIG. 4 is a side view of a distal end portion an exemplary plunger rod assembly in accordance with one embodiment.

FIG. 4 depicts another example of a plunger rod assembly 400 that includes a plunger rod 418 and a threaded member 408. The threaded member 408 is compatible with the stopper 300 of FIG. 3. The distal end portion 402 includes a stem 404 and a threaded member 408 distal to the stem 404. The threaded member 408 of FIG. 4 has a barbed, helical male thread. The threaded member 408 has a shorter thread length (L4) compared to the thread length (L2) of the threaded member 208 of FIG. 2B. In some embodiments, the threaded member 408 includes a maximum major diameter (MMD) near its proximal end. The maximum major diameter of the helical male thread may form a crest peak 412 and a proximal transitional threaded region 416 for engaging with an inner wall of an inner cavity of a stopper such that a plunger rod remains coupled to a stopper during use. It is to be appreciated that the threaded member may include a variable major diameter, which means that the major diameter of the threaded member changes along a longitudinal axis defined by the plunger rod of the plunger rod assembly.

Referring now to FIGS. 5A and 5B, exemplary plunger rod assembly 500 includes a variable, threaded member 508 with multiple crest peaks 512, 513. The plunger rod assembly 500 is similar to the plunger rod assembly 200 of FIG. 2A, with the exception of the design of the threaded member 508.

The threaded member 508 includes a variable major diameter that varies along a longitudinal axis (X1) of the plunger rod assembly 500. In addition, the threaded member 508 can include a helical male thread that includes a middle portion, a proximal end and a distal end. The threaded member 508 may also include two crest peaks 512, 513 in the middle portion, where each crest peak 512, 513 defines a maximum major diameter (MMD). Each crest peak 512, 513 therefore has a major diameter that is larger than the adjacent portions of the threaded member 508. The threaded member 508 may include a crest valley 520 between the two crest peaks 512, 513 that defines a minimum diameter of the threaded member 508. In some embodiments, the threaded member 508 can have more than two crest peaks 512, 513. For example, the threaded member 508 may have one, two, three, four, five, or six or more crest peaks. Adjacent each crest peak 512, 513 may be a distal and a proximal transitional threaded region 514, 516, respectively. At least one of the proximal transitional threaded regions 514, 516 may engage with an inner wall of an inner cavity of a stopper, such that the plunger rod assembly 500 remains coupled to the stopper during use in a non-threaded engagement. Increasing the number of proximal transitional threaded regions 514, 516 within the threaded member 508 can increase the number of engagement points between the stopper and the threaded member 508, as well as the maximum retention force between the stopper and a plunger rod assembly 500.

Referring to FIG. 6, a stopper 600 is depicted that is compatible, for example, with the plunger rod assembly 500 shown in FIGS. 5A and 58B. The stopper 600 may include an elastomeric body 602 having a distal end and a proximal end. The elastomeric body 602 may be defined by an exterior surface and an interior surface that defines an inner cavity 606 of the stopper 600. The inner cavity 606 may be a non-threaded cavity having smooth inner walls configured to engage a threaded member of a plunger rod assembly in a non-threaded engagement. The stopper 600 has an exterior surface that may include a plurality of outwardly extending ribs 604 for engaging a syringe barrel. The ribs 604 allow the elastomeric body 602 to slidably move within a barrel of a syringe with reduced frictional drag in one or more directions. Because the ribs 604 of the stopper 600 can elastically deform, the stopper 600 may be inserted inside a barrel of a syringe and slidably move within the barrel despite the ribs 604 having a larger diameter than the diameter of the inside of the barrel, which may be lubricant-free.

Still referring to FIG. 6, the inner cavity 606 of the stopper 600 may be sized and shaped to receive a threaded member of a plunger rod assembly, such as the threaded member 508 depicted in FIGS. 5A and 5B. As will be described in greater detail hereafter, the inner cavity 606 of the stopper 600 may be a non-threaded cavity defined by smooth inner walls configured to engage the threaded member, such as the threaded member 508, at multiple locations within the inner cavity 606.

The inner cavity 606 may be defined, in some embodiments, by at least two necked regions 620 and at least two expanded regions 622. Each necked region 620 may be connected to an expanded region 622 by a transitional walls 624, 626. The transitional walls 624, 626 may have a smooth, inner surface that tapers from a larger inner diameter to a smaller inner diameter. In some embodiments, the transitional walls 624, 626 may be a smooth, inner surface region that increases from a smaller inner diameter to a larger inner diameter. In some embodiments, the transitional walls 624, 626 may be shaped like a frustum cone (e.g., generally frustoconical).

In some embodiments, one or more of the transitional walls 624,626 of the plunger 600 may engage with a threaded member to retain the threaded member within the inner cavity 606 of the stopper 600 while the stopper 600 slides proximally within a syringe barrel. In some embodiments, one or more of the transitional walls 624, 626 of the stopper 600 may engage with a threaded member when the stopper 600 is actuated by a plunger rod assembly to slide distally in a syringe barrel. As shown in FIG. 6, each expanded region 622 is adjacent to a proximal transitional wall 624 and a distal transitional wall 626. In some embodiments, one or more proximal transition walls 624 may engage with a threaded member to retain the threaded member within the inner cavity 606 when the stopper 600 is sliding proximally in a syringe barrel. In some embodiments, one or more distal transitional walls 626 of the stopper 600 can engage with a threaded member when the stopper 600 slides distally within a syringe barrel. The inner cavity 606 may have one, two, three, four, five, six, or six or more necked and expanded regions 620, 622, respectively. Accordingly, the inner cavity 606 may have one, two, three, four, five or six or more proximal and/or distal transitional walls 624, 626 to increase engagement between a threaded member and the stopper 600.

In some embodiments, an angle (a) of the proximal or the distal transitional wall 624, 626 relative to a central axis (X2) of the stopper 600 can be complementary to the shape of the distal end portion of a plunger rod assembly, for example, a threaded member, such as threaded member 508. In some embodiments, the angle (a) of the proximal or distal transitional wall 624, 626 may be complementary to the angle of the proximal or distal transitional threaded region, respectively, of a threaded member. For example, in some embodiments, the angle (a) of the proximal or distal transitional wall 624, 626 with respect to the central axis (X2) of the stopper 600 may range from about 5 degrees to about 90 degrees, from about 5 degrees to about 40 degrees, from about 10 degrees to about 30 degrees, from about 15 degrees to about 20 degrees, from about 15 degrees to about 20 degrees, from about 5 degrees to about 10 degrees, from about 10 degrees to about 20 degrees, from about 15 degrees to about 25 degrees, from about 20 degrees to about 25 degrees, from about 30 degrees to about 40 degrees, from about 5 degrees to about 15 degrees, from about 5 degrees to about 20 degrees, from about 5 degrees to about 25 degrees, from about 5 degrees to about 30 degrees, from about 5 degrees to about 40 degrees, from about 10 degrees to about 20 degrees, from about 15 degrees to about 25 degrees, from about 10 degrees to about 40 degrees, from about 20 degrees to about 30 degrees, from about 20 degrees to about 40 degrees, from about 30 degrees to about 40 degrees, from about 40 degrees to about 50 degrees, from about 50 degrees to about 60 degrees, from about 60 degrees to about 70 degrees, from about 70 degrees to about 80 degrees, or from about 80 degrees to about 90 degrees.

In some embodiments, the length (Lt) of the proximal and/or distal transitional wall 624, 626 may range from about 0 mm to about 20 mm, from about 1 mm to about 15 mm, from about 1 mm to about 10 mm, from about 1 mm to about 5 mm, from about 1 mm to about 3 mm, from about 1 mm to about 2 mm, or from about 1 mm to about 1.3 mm.

In addition, the inner cavity 606 of the stopper 600 may defined by at least two adjacent pairs of frustoconical inner surfaces: a first pair of frustoconical inner surfaces 632 and a second pair of frustoconical inner surfaces 630 connected to the opening 612. In some embodiments, the inner cavity 606 includes more than two pairs of frustoconical inner surfaces, e.g., a third, fourth, or fifth pair (or more) of frustoconical inner surfaces. Each pair of frustoconical inner surfaces includes a proximal frustoconical inner surface 608 and a distal frustoconical inner surface 610. The frustoconical inner surfaces 608, 610 of each pair of frustoconical inner surfaces 630, 632 may be oriented to join each other at their larger termination ends. Each pair of frustoconical inner surfaces 630, 632 may be located adjacent to another pair of frustoconical inner surfaces 630, 632. For example, the first pair of frustoconical inner surfaces 630 may be located proximal to the second pair of frustoconical inner surfaces 632. The proximal or distal frustoconical inner surfaces 608, 610 of each pair 630, 632 can provide an engagement surface (i.e. engagement feature) for retaining the threaded member of the plunger rod assembly. The engagement surface can be defined with the angles and lengths provided herein for the proximal and distal transitional walls 624, 626.

Figure 7B:
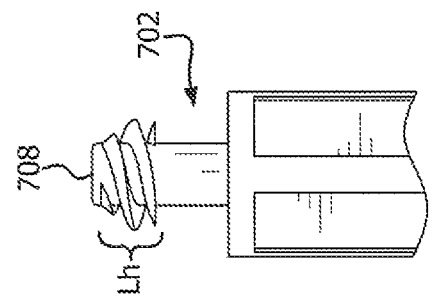
FIG. 7B is a magnified view of the distal end portion of the plunger rod assembly of FIG. 7A in accordance with at least one embodiment.
Figure 7A:
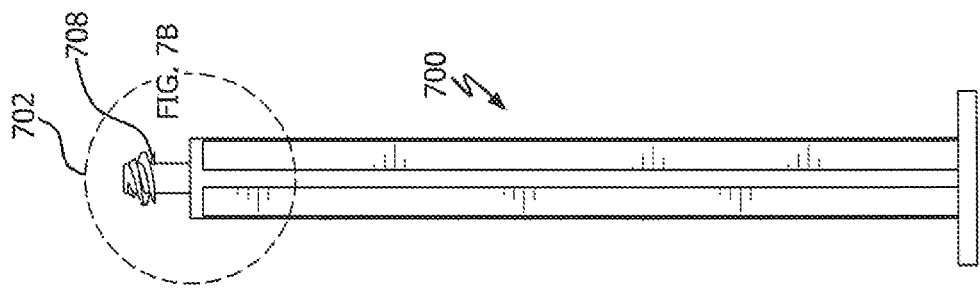
FIG. 7A is a side view of an exemplary plunger rod assembly in accordance with at least one embodiment.

Referring to FIGS. 7A and 7B, another exemplary plunger rod assembly 700 is depicted. Plunger rod assembly 700 may be compatible with the stopper 600 shown in FIG. 6. The plunger rod assembly 700 is similar to the plunger rod assemblies described herein, with exception of the design of a threaded member 708. In some embodiments, as shown in FIG. 7B, the threaded member 708 may include a helical male thread having a short thread length (Lh) compared to the thread length of the helical male thread of the plunger rod assembly 500 depicted in FIGS. 5A and 5B. The threaded member 708, when fully seated within an inner cavity of a stopper, may engage the engagement surfaces of the stopper, such as the proximal frustoconical inner surface 608 of the second pair of frustoconical inner surfaces 632, or the most distal, proximal transitional inner wall 624 the plunger 600 of FIG. 6.

Figure 8B:
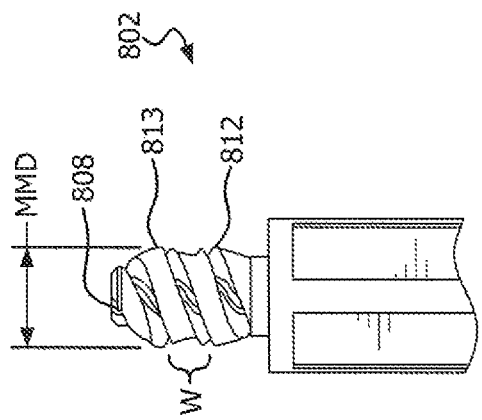
FIG. 8B is a magnified view of the distal end portion of the plunger rod assembly of FIG. 8A in accordance with at least one embodiment.
Figure 8A:
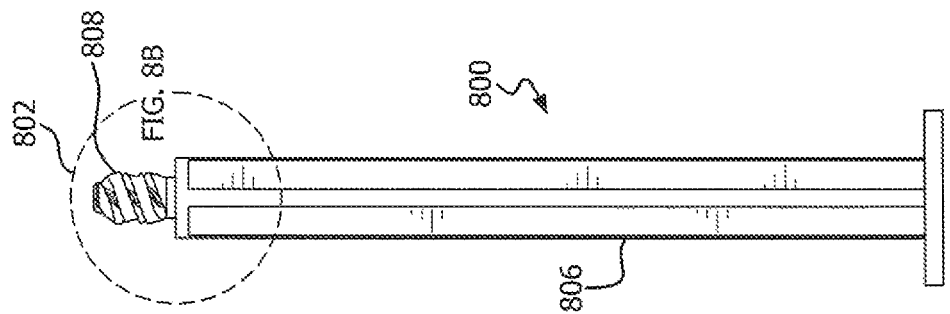
FIG. 8A is a side view of an exemplary plunger rod assembly in accordance with at least one embodiment.

Referring to FIGS. 8A and 8B, another exemplary plunger rod assembly 800 is illustrated. The plunger rod assembly 800 may be compatible with the stopper 600 depicted in FIG. 6. The plunger rod assembly 800 is similar to the plunger rod assemblies provided herein (e.g., plunger rod assembly 500 shown in FIG. 5) with exception of the design of the threaded member 808. The threaded member 808 of FIGS. 8A and 8B includes a helical male thread having a larger thread width (w) and smaller thread profile (i.e., smaller MMD) compared to the thread width (w) and thread profile of threaded member 508 depicted in FIGS. 5A and 5B. Threaded member 808 may include two crest peaks 812, 813 defined by two MMD points along the threaded member 808. Portions of the threaded member 808 just proximal to each crest peak 812, 813 may engage with an engagement surface of the stopper, such as the proximal frustoconical inner surface 608 of the second pair of frustoconical inner surfaces 632, or the most distal, proximal transitional inner wall 624 the plunger 600 shown in FIG. 6. When threaded member 808 is retracted from a stopper with a force that exceeds a predetermined maximum retention force, the portion of the threaded member 808 that is engaged with the stopper can elastically deform the stopper, thereby allowing the threaded member to pass through an opening in the stopper and, ultimately, disconnecting the plunger rod assembly from the stopper.

For proper engagement of the plunger rod assembly with the stopper, the stopper is inserted into the syringe barrel such that the opening of the stopper is centered within the syringe barrel to allow proper alignment with a plunger rod assembly. Typically, the syringes are prefilled with a liquid, such as a medicament, and the stopper is inserted into or over the liquid. In automated systems, a vent tube and an insertion pin may be used in combination to insert the stopper into the syringe barrel with little to no distortion, buckling, or wrinkling of the stopper. The vent tube allows a stopper to be placed inside a syringe barrel without over-pressurizing the liquid contained therein. In exemplary embodiments, the vent tube is slightly smaller than the diameter of the syringe barrel, thereby allowing air to escape as the stopper is placed inside the barrel. The placement of the stopper in the syringe barrel may be conducted using conventional vacuum or vacuum with an insertion pin insert.

In use, a stopper is positioned in a within the vent tube. Once the stopper is positioned in the vent tube, an insertion pin moves the stopper through the vent tube to position the stopper in the syringe barrel. The tip of the insertion pin interfaces with the cavity of the stopper to enable the stopper to be inserted straight and with minimal buckling into the syringe barrel.

Figure 9A:
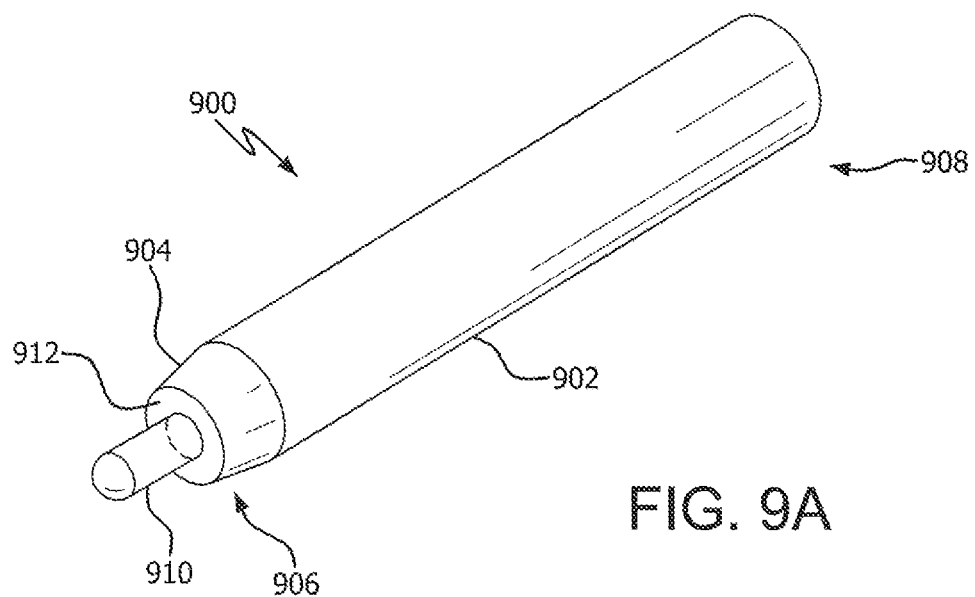
FIG. 9A is an isometric view of an insertion pin in accordance with at least one embodiment.
Figure 9B:
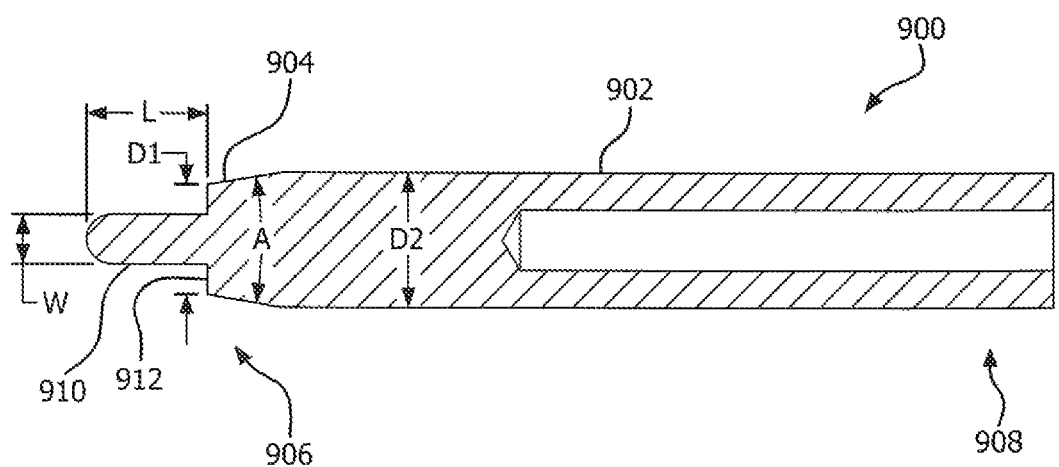
FIG. 9B is a cross-sectional view of the insertion pin of FIG. 9A.

An exemplary insertion pin for use with the plunger bodies described herein is set forth in FIGS. 9A and 9B. The insertion pin 900 includes a generally cylindrical body 902 having a proximal end 906 and a distal end 908. The body 902 has a diameter that is slightly smaller than the vent tube inner diameter (04) at the proximal of the body (shown in FIG. 10B). The proximal end 906 interfaces with the cavity of the stopper. The distal end 908 may be sized to mate with a mechanical drive used to push the insertion pin through a vent tube.

The insertion pin 900 also includes a tapered region 904 at the proximal end 906 that interconnects a tip end 910 and the body 902. The tip end 910 is designed to fit in the cavity of a stopper. In at least one embodiment, the insertion pin tip end 910 is disengageable from the body 902. The tapered region 904 tapers from the flat surface 912 to the body 902 at an angle (A) from about 10 degrees to about 30 degrees, from about 20 degrees to about 30 degrees, from about 15 degrees to about 25 degrees, from about 10 degrees to about 20 degrees, from about 20 degrees to about 25 degrees. Additionally, the tapered region 904 has a higher clearance than a vent tube so as to avoid pinning the distal end of a stopper between the wall of the syringe and the insertion pin 900. The flat surface 912 is designed to push against the distal end of a stopper to provide straightness and stability during insertion of the stopper into the syringe barrel. The flat surface 912 has a diameter (D1) that may be from about 2 mm to about 6 mm, from about 2.5 mm to about 5 mm, or from about 2.8 mm to about 4 mm. It is to be appreciated that the tapered region 904 may include or be formed of shapes other than a straight taper (e.g. linear), such as, for example, curvilinear, rounded, radiused, multiple tapers etc. (not illustrated).

The tip end 910 has a length (L1) that may be approximately the depth of the inner cavity of the stopper. In exemplary embodiments, the plunger end 910 has a length from about 3 mm to about 8 mm, from about 4 mm to about 7 mm, from about 4.5 mm to 5.5 mm, or from about 5 mm to about 6 mm. In addition, the plunger end 910 may have a width (W) from about 0.5 mm to about 5 mm, from about 1 mm to about 4 mm, from about 1 mm to about 3 mm, from about 2 mm to about 3 mm, or from about 1.5 mm to about 2.5 mm. The combination of the diameter (D1) and length (L1) of the tip end 910 creates a volume that is compatible with the cavity of the stopper during insertion. In some embodiments, the tip end 910 has a rounded end, or "bottle-nose" appearance.

The body 902 has a diameter (D2) that may range from about 3 mm to about 8 mm, from about 3.5 mm to about 7 mm, from about 4 mm to about 6 mm, from about 5 mm to about 6 mm, from about 5 mm to about 5.5 mm, or from about 5.5 to about 6 mm. The body 902, as well as the stopper end 910 may be formed from a polymeric material such as poylyether ether ketone (PEEK), polytetrafluoroethylene (PTFE), expanded polytetrafluoroethylene (ePTFE), or other materials such as stainless steel.

Figure 10A:
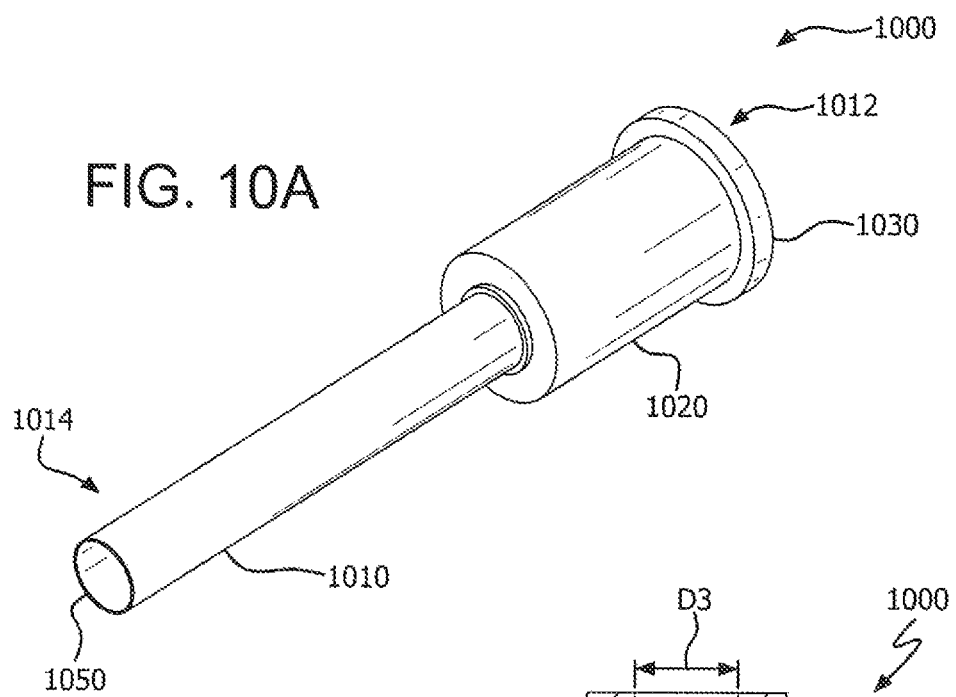
FIG. 10A is an isometric view of a vent tube according to an exemplary embodiment.
Figure 10B:
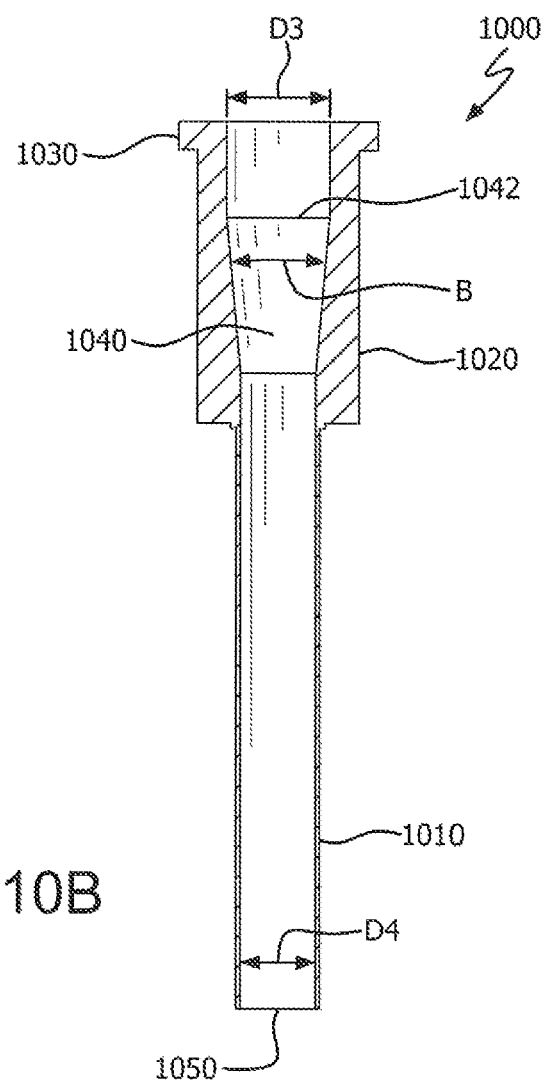
FIG. 10B is a cross-sectional view of the vent tube of FIG. 10A.

Turning to FIGS. 10A and 10B, an exemplary vent tube is depicted that can be used with the insertion pin 900 described above. The vent tube 1000 has a proximal end 1012 and a distal end 1014. The vent tube 1000 includes a body 1010 and a machine adaptor 1020. An alignment flange 1030 protrudes from the end of the machine adaptor 1020. The alignment flange 1030 has a shape that is sufficient to align with auxiliary equipment on a filling line. As shown in FIG. 10B, the body 1010 contains a transition zone 1040 at the distal end thereof. The body 1010 is the section of the vent tube 1000 that fits within the syringe barrel and allows the stopper to be placed into a syringe barrel. The body 1010 is sized smaller than the inner diameter of the barrel to allow air space between the outside of the vent tube 1000 and the syringe barrel. Air is able to escape along the path created by the smaller sizing of the body 1010 compared to the syringe to avoid over-pressurization of the liquid within the syringe barrel.

The transition zone 1040 is where the stopper is compressed from its diameter in the placement region 1042 to a diameter sufficient to pass through the distal opening 1050 of the vent tube 1000. Thus, the diameter of the stopper is reduced from D3 (diameter at the proximal end of the body 1010) to D4 (diameter at the distal end of the body 1010). The transition zone 1040 tapers from the flat surface of the placement region 1042 to the body 1010 at a taper angle (B) that is from about 1 degree to about 20 degrees, from about 3 degrees to about 15 degrees, from about 5 degrees to about 10 degrees, from about 10 degrees to about 15 degrees. The placement region 1042 has a flat surface or a substantially flat surface and a diameter from about 3 mm to about 20 mm, from about 5 mm to about 15 mm, from about 7 mm to about 10 mm, from about 7.0 mm to about 8.0, or from about 7.5 mm to about 8.0 mm. In addition, the placement region 1042 may be sized to be slightly larger than the diameter of the largest outer rib of the stopper unless the stopper is pre-compressed.

The syringes described herein and components thereof can be fabricated using various processes. In some embodiments, injection molding may be used to fabricate the syringe components provided herein. Other suitable processes can include, but are not limited to, extrusion, compression molding, solvent casting and combinations thereof.

It is to be appreciated that the ranges described herein may be utilized in conjunction with a 0.5 ml or 1 ml long syringe assembly, but may be appropriately scaled to smaller or larger syringes. It should also be understood that one or more design features of the syringes described herein can be combined with other features of other syringes described herein. In effect, hybrid designs that combine various features from two or more of the syringe designs provided herein can be created, and are considered to be within the scope of this disclosure.

In another aspect, the medical delivery device, plunger rod, and stopper described herein may be used in combination different therapeutic compounds such as, for example, drugs and biologics, including but not limited to, antibodies, antisense, RNA interference, gene therapy, primary and embryonic stem cells, vaccines, and combinations thereof. For instance, the embodiments described herein may be utilized in combination with any or all of the following:

Cell therapy using cells that are derived primarily from endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands, and urogenital tract), Extracellular matrix cells, Contractile cells, Blood and immune system cells, Germ cells, Nurse cell, Interstitial cells or a combination thereof. Additionally cells that are genetically, chemically or physically altered or modified are considered to be in the scope of the invention.

Examples of Exocrine secretory epithelial cells include, but are not limited to, Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II pneumocyte of lung, Clara cell of lung; Hormone-secreting cells including but not limited to: Anterior pituitary cells, Intermediate pituitary cell, Magnocellular neurosecretory cells, Gut and respiratory tract cells, Thyroid gland cells, Parathyroid gland cells, Adrenal gland cells, Leydig cell of testes secreting testosterone, Theca intema cell of ovarian follicle secreting estrogen, Corpus luteum cell of ruptured ovarian follicle secreting progesterone, Juxtaglomerular cell, Macula densa cell of kidney, Peripolar cell of kidney, Mesangial cell of kidney, Pancreatic islets; Keratinizing epithelial cells including but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell; Wet stratified barrier epithelial cells including but not limited to: Surface epithelial cell of stratified squamous epithelium and basal cell of epithelia of cornea, tongue, oral cavity, esophagus, anal canal, distal urethra and vagina, Urinary epithelium cell; Sensory transducer cells including but not limited to: Auditory inner hair cell of organ of Corti, Auditory outer hair cell of organ of Corti, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye: Proprioceptive primary sensory neurons, Touch-sensitive primary sensory neurons, Type I carotid body cell, Type II carotid body cell, Type I hair cell of vestibular system of ear, Type II hair cell of vestibular system of ear, Type I taste bud cell; Autonomic neuron cells including but not limited to: Cholinergic neural cell, Adrenergic neural cell, Peptidergic neural cell; Sense organ and peripheral neuron supporting cells including but not limited to: Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell, Enteric glial cell; Central nervous system neurons and glial cells including but not limited to: Astrocyte, Neuron cells, Oligodendrocyte, Spindle neuron; Lens cells including but not limited to: Anterior lens epithelial cell, Crystallin-containing lens fiber cell; Metabolism and storage cells including but not limited to: Adipocytes: Liver lipocyte; Barrier function cells including but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nonciliated cell, Epididymal principal cell, Epididymal basal cell; Extracellular matrix cells including but not limited to: Ameloblast epithelial cell, Planum semilunatum epithelial cell of vestibular system of ear, Organ of Corti interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementoblast/cementocyte, Odontoblast/odontocyte, Hyaline cartilage chondrocyte, Fibrocartilage chondrocyte, Elastic cartilage chondrocyte, Osteoblast/osteocyte, Osteoprogenitor cell, Hyalocyte of vitreous body of eye, Stellate cell of perilymphatic space of ear, Hepatic stellate cell, Pancreatic stelle cell; Contractile cells including but not limited to: Skeletal muscle cell, Satellite cell, Heart muscle cells, Smooth muscle cell, Myoepithelial cell of iris, Myoepithelial cell of exocrine glands; Blood and immune system cells including but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system; Germ cells including but not limited to: Oogonium/Oocyte, Spermatid, Spermatocyte, Spermatogonium cell, Spermatozoon; Nurse cell including but not limited to: Ovarian follicle cell, Sertoli cell, Thymus epithelial cell; Interstitial cells including but not limited to: Interstitial kidney cells and a combination thereof.

Examples of antibodies, antisense, RNA interference, or gene therapy made to protein targets or gene(s) of: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-terminal-binding protein 1, Structural maintenance of chromosomes protein 1A; Esterases; Phosphatases; Examples of Ion channels include but are not limited to: ligand-gated ion channels, voltage-gated ion channels; Examples of growth factors include but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), b, one morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), Insulin-like growth factors; Examples of G Protein-Coupled Receptors (GPCR) include but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C—C motif) receptor family, Sphingosine 1-phosphate receptor family, Succinic receptor, Cholinergic receptor family. Chemokine-like receptor family, Cannabinoid receptor family, Corticotropin releasing hormone receptor family, prostaglandin D2 receptor, Chemokine C-X3-C receptor family, Chemokine (C—X—C motif) receptor family, Burkitt lymphoma receptor, Chemokine (C—X—C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides BNV receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin I2 (prostacyclin) receptor family, Parathyroid hormone receptor family, muscarinic 4 (rM4), Prostanoid DP2 receptor (rGPR44), Prokineticin receptor family, Relaxin family peptide receptor family, Secretin receptor (secretin), Smoothened, Frizzled class receptor (Smoothened), trace amine associated receptor family, Tachykinin family, Thromboxane A2 receptor (TP), Thyrotropin-releasing hormone receptor (TRH1), Thyroid Stimulating Hormone Receptor (TSH); Examples of Protein kinases include but are not limited to: AP2 associated kinase, Homo sapiens ABL proto-oncogene 1—non-receptor tyrosine-protein kinase family, c-abl oncogene 1 receptor tyrosine kinase family, v-abl Abelson murine leukemia viral oncogene homolog 2, activin A receptor family, chaperone—ABC1 activity of bcl complex homolog (S. pombe) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family—SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (S. pombe) (CHEK1), CHK2 checkpoint homolog (S. pombe) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family—Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoletic cell kinase (HCK), homeodomain interacting protein kinase family, mitogen-activated protein kinase kinase kinase kinase family, hormonally up-regulated Neu-associated kinase (HUNK), intestinal cell (MAK-like) kinase (ICK), Insulin-like growth factor 1 receptor (IGF1R), conserved helix-loop-helix ubiquitous kinase (IKK-alpha), inhibitor of kappa light polypeptide gene enhancer in B-cells—kinase beta family, insulin receptor (INSR), insulin receptor-related receptor (INSRR), interleukin-1 receptor-associated kinase family, 1L2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/threonine kinase family leucine-rich repeat kinase family, v-yes-1 Yamaguchi sarcoma viral related oncogene homolog (LYN), male germ cell-associated kinase (MAK), MAP/microtubule affinity-regulating kinase family, microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family, Spleen tyrosine kinase (SYK), TAO kinase family, TANK-binding kinase 1 (TBK1), tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), zeta-chain (TCR) associated protein kinase 70 kDa (ZAP70); Examples of nuclear hormone receptors include but are not limited to: Androgen receptor (AR), Estrogen related receptor alpha (ESRRA), Estrogen receptor 1 (ESR1), Nuclear receptor subfamily 1—group H—member 4 (NR1H4), Nuclear receptor subfamily 3—group C—member 1 (glucocorticoid receptor) (NR3C1), Nuclear receptor subfamily 1—group H—member 3 (Liver X receptor α) (NR1H3), Nuclear receptor subfamily 1—group H—member 2 (Liver X receptor β) (NR1H2), Nuclear receptor subfamily 1—group H—member 2 (Liver X receptor β) (NR1H2), Nuclear receptor subfamily 3—group C—member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor α (PGR), Progesterone receptor β (PGR), Retinoic acid receptor—alpha (RARA), Retinoic acid receptor—beta (RARB), Retinoid X receptor—alpha (RXRA), Retinoid X receptor—gamma (RXRG), Thyroid hormone receptor—alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, Nerve growth factor-induced-B, Germ cell nuclear factor; Examples of Epigenetic targets include but are not limited to: ATPase family AAA domain-containing protein 2 (ATAD2A), ATPase family—AAA domain containing 2B (ATAD2B), ATPase family AAA domain containing—2B (ATAD2B), bromodomain adjacent to zinc finger domain—1A (BAZ1A), bromodomain adjacent to zinc finger domain—1B (BAZIB), bromodomain adjacent to zinc finger domain—2A (BAZ2A), bromodomain adjacent to zinc finger domain—2A (BAZ2A), bromodomain adjacent to zinc finger domain—2B (BAZ2B), bromodomain-containing protein 1 (BRD1), Bromodomain containing protein 2-1st bromodomain (BRD2), Bromodomain containing protein 2-1st & 2nd bromodomains (BRD2), bromodomain-containing protein 2 isoform 1—bromodomain 2 (BRD2(2)), bromodomain-containing protein 3—bromodomain 1 (BRD3(1)), Bromodomain-containing protein 3-1st bromodomain (BRD3), Bromodomain-containing protein 3-1st & 2nd bromodomains (BRD3), bromodomain-containing protein 3—bromodomain 2 (BRD3(2)), Bromodomain containing protein 4-1st bromodomain (BRD4), bromodomain-containing protein 4 isoform long—bromodomains 1 and 2 (BRD4(1-2)), bromodomain-containing protein 4 isoform long—bromodomain 2 (BRD4(2)), bromodomain-containing protein 4 isoform short (BRD4(full-length-short-iso.)), Bromodomain containing protein 7 (BRD7), bromodomain containing 8—bromodomain 1 (BRD8(1)), bromodomain containing 8—bromodomain 2 (BRD8(2)), bromodomain-containing protein 9 isoform 1 (BRD9), Bromodomain containing testis-specific—1st bromodomain (BRDT), Bromodomain containing testis-specific—1st & 2nd bromodomains (BRDT), bromodomain testis-specific protein isoform b—bromodomain 2 (BRDT(2)), bromodomain and PHD finger containing—1 (BRPF1), bromodomain and PHD finger containing—3 (BRPF3), bromodomain and PHD finger containing—3 (BRPF3), Bromodomain and WD repeat-containing 3-2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase—KAT2A (GCN5L2), Euchromatic histone-lysine N-methyltransferase 1 (EHMT1), Histone-lysine N-methyltransferase MLL (MLL), Polybromo 1-1st bromodomain (PB1(1)), Polybromo 1-2nd bromodomain (PB1(2)), polybromo 1—bromodomain 2 (PBRM1(2)), polybromo 1—bromodomain 5 (PBRM1(5)), Histone acetyltransferase KAT2B (PCAF), PH-interacting protein—1st bromodomain (PHIP(1)), PH-interacting protein—2nd bromodomain (PHIP(2)), Protein kinase C-binding protein 1 (PRKCBP1), Protein arginine N-methyltransferase 3 (PRMT3), SWI/SNF related—matrix associated—actin dependent regulator of chromatin—subfamily a—member 2 (SMARCA2), SWI/SNF related—matrix associated—actin dependent regulator of chromatin—subfamily a—member 4 (SMARCA4), Nuclear body protein—SP110 (SP110), Nuclear body protein—SP140 (SP140), Transcription initiation factor TFIID subunit 1 (TAF1(1-2)), TAF1 RNA polymerase II—TATA box binding protein (TBP)-associated factor—250 kDa—bromodomain 2 (TAF1(2)), Transcription initiation factor TFIID subunit 1-like—1st bromodomain (TAF1L(1)), Transcription initiation factor TFIID subunit 1-like—2nd bromodomain (TAF1L(2)), tripartite motif containing 24 (TRIM24(Bromo.)), tripartite motif containing 24 (TRIM24 (PHD-Bromo.)), E3 ubiquitin-protein ligase TRIM33 (TRIM33), tripartite motif containing 33 (TRIM33(PHD-Bromo.)), WD repeat 9-1st bromodomain (WDR9(1)), WD repeat 9-2nd bromodomain (WDR9(2)); membrane transport proteins including but not limited to ATP-binding cassette (ABC) superfamily, solute carrier (SLC) superfamily, multidrug resistance protein 1 (P-glycoprotein), organic anion transporter 1, and protein such as EAAT3, EAAC1, EAAT1, GLUT1, GLUT2, GLUT, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGCI, ARALAR, Citrin, STLN2, aralar2, TPC, MUP1, MCPHA, CACT, GC1, PHC, DTD, CLD, DRA, PDS, Prestin, TATI, FATP4, ENT3, ZnT2, ZnT10, ATI, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATPIB1, OATP1B3, OATP2A1; structural proteins including but not limited to tubulin, heat shock protein, Microtubule-stabilizing proteins, Oncoprotein 18, stathmin, kinesin-8 and kinesin-14 family, Kip3, Kif18A; proteases including but not limited ADAM (a disintegrin and metalloprotease) family; Other molecule targets in signal transductions include but are not limited to: Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), Catenin (cadherin-associated protein), beta 1 (CTNNBI), and combinations thereof.

Examples of known biologics include but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-Cide, HumaSPECT, HuMax-CD4, HuMax-EGFr, Humira, HuZAF, Hybri-ceaker, Ilaris, Indimacis-125, Kadcyla, Lemtrada, LeukArrest, LeukoScan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Solids, Stelara, Synagis, Tactress, Theracim, Theragyn, Theraloc, Tysabri, Vectibix, Verluma, Xolair, Yervoy, Zenapax, and Zevalin or combinations thereof.

Examples of known Monoclonal antibodies include but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fuiranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, LBR-101/PF0442g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Namilumab, Naptumomab estafenatox, Naratuximab emtansine, Namatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimumab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralizumab, and Zolimomab aritox or combinations thereof.

Examples of vaccines developed for viral diseases include but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, *Yersinia pestis* vaccine; Examples of parasitic diseases include but are not limited to: Malaria vaccine, Schistosomiasis vaccine, Chagas disease vaccine, Hookworm vaccine, Onchocerciasis river blindness vaccine for humans, Trypanosomiasis vaccine, Visceral leishmaniasis vaccine; Examples of non-infectious diseases include but are not limited to: Alzheimer's disease amyloid protein vaccine, Breast cancer vaccine, Ovarian cancer vaccine, Prostate cancer vaccine, Talimogene laherparepvec (T-VEC); also vaccines including but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, MenHibrix, Menomune-A/C/Y/W-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TENIVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), [0137], Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan HcI Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX40L, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Camitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Affa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalamin for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), Depo-Cyt (Cytarabine Liposome Injection), DepoDur (Morphine Sulfate XR Liposome Injection), Desmopressin Acetate Injection (DDAVP Injection), Depo-Estradiol, Depo-Provera 104 mg/ml, Depo-Provera 150 mg/ml, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscamet Sodium Injection (Foscavir), Foscavir (Foscamet Sodium Injection), Fosphenytoin Sodium Injection (Cerebyx), Fospropofol Disodium Injection (Lusedra), Fragmin, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), lobenguane 1123 Injection for Intravenous Use (AdreView), lopromide Injection (Ultravist), loversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecaliantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Palifermin), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocamitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprew), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pamidronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGintron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Scierostin Ab, Sensipar (cinacalcet), Sensorcaine (Bupivacaine HCl Injections), Septocaine (Articane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intraarticular Injection), Tarceva, Taxotere (Docetaxel for Injection), Technetium Tc 99m, Telavancin for Injection (Vibativ), Temsirolimus Injection (Torisel), Tenormin I.V.

Injection (Atenolol Inj), Teriparatlde (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprew (Olanzapine Extended Release Injectable Suspension) and a combination thereof.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A plunger assembly comprising:
   a stopper comprising an elastomeric body, said stopper including:
      an exterior surface; and
      a non-threaded inner cavity, said inner cavity having a generally frustoconic shape and an engagement surface; and
   a plunger rod having a threaded member at a plunger-engaging end,
      wherein said stopper and said plunger rod are directly coupled together in an integrated, non-threaded engagement such that said plunger rod is freely rotatable and said threaded member is retained within said inner cavity when said stopper and said plunger rod are directly coupled together.

2. The plunger assembly of claim 1, wherein said exterior surface comprises a plurality of outwardly extending ribs for engagement with a syringe barrel.

3. The plunger assembly of claim 1, wherein said threaded member is rotatable within said inner cavity.

4. The plunger assembly of claim 1, wherein a portion of said inner cavity comprises at least one non-engaging surface that does not contact said threaded member.

5. The plunger assembly of claim 1, wherein said inner cavity comprises a plurality of engagement surfaces and non-engaging surfaces.

6. The plunger assembly of claim 5, wherein each said engagement surface is spaced apart from one another.

7. The plunger assembly of claim 1, wherein said threaded member contacts said engagement surface to support said plunger rod in an integrated, non-threaded engagement with said stopper.

8. The plunger assembly of claim 1, wherein, said threaded member contacts said engagement surface to support the plunger rod in said integrated, non-threaded engagement.

9. A syringe assembly comprising:
   a cylindrical barrel having a smooth internal surface; and
   a plunger assembly inserted into a receiving end of said cylindrical barrel, said plunger assembly comprising:
      a stopper comprising an elastomeric body, said stopper including:
         an exterior surface having plurality of outwardly extending ribs for engagement with said cylindrical barrel;
         a non-threaded inner cavity, said inner cavity having at least one generally frustoconical portion and at least one engagement surface; and
      a plunger rod having a threaded member at a plunger-engaging end,
         wherein said threaded member contacts said engagement surface of said inner cavity to support said plunger rod in an integrated, non-threaded engagement with said stopper, and
         wherein said plunger rod is freely rotatable and said threaded member is retained within said inner cavity when said stopper and said plunger rod are directly coupled together.

10. A plunger assembly for a fluid dispensing syringe, the plunger assembly comprising:
   a plunger rod having a distal end comprising a threaded member, the threaded member including a variable major diameter; and
   a stopper comprising an elastomeric body including a distal end and a proximal end, the stopper defining a non-threaded inner cavity that includes first and second frustoconical inner surfaces connected to an opening, each said frustoconical inner surface being oriented to adjoin each other at a large termination end;
wherein at least one of the frustoconical inner surfaces is configured to engage the threaded member,
wherein said plunger rod is directly coupled to said stopper in an intergrated non-threaded engagement, and
wherein said plunger rod is freely rotatable and said threaded member is retained within said inner cavity when said stopper and said plunger rod are directly coupled together.

11. The plunger assembly of claim 10, wherein the inner cavity is sized and shaped to receive the threaded member.

12. The plunger assembly of claim 10, wherein the inner cavity comprises a shape that is generally complementary to the shape of the threaded member.

13. The plunger assembly of claim 10, wherein the inner cavity has smooth inner walls configured to engage the threaded member.

14. The plunger assembly of claim 10, wherein the first frustoconical inner surfaces are located proximal to the second frustoconical inner surfaces and are distal to the opening.

15. The plunger assembly of claim 10, wherein each frustoconical inner surface comprises a small termination end, a large termination end, and a tapered surface extending between the small and large termination ends.

16. The plunger assembly of claim 10, wherein the first and second frustoconical inner surfaces form an abutment having an inner diameter that is larger than a maximum diameter of the inner cavity.

17. The plunger assembly of claim 10, wherein the first and second frustoconical inner surfaces together form a hexagonal shaped inner cavity within the plunger.

18. The plunger assembly of claim 10, wherein the first and second frustoconical inner surfaces, provide an engagement region for engaging the threaded member.

19. The plunger assembly of claim 10, wherein the first frustoconical surfaces of the plunger engage with the threaded member to retain the threaded member within the inner cavity of the plunger.

20. The plunger assembly of claim 10, wherein threaded regions of the threaded member form a tapered profile that seats against the first and second frustoconical inner surfaces.

21. The plunger assembly of claim 10, wherein the threaded member is retracted from a plunger with a force that is equal to or greater than a predetermined maximum retention force.

* * * * *